(12) United States Patent
Aubrun-Sonneville et al.

(10) Patent No.: US 7,153,498 B2
(45) Date of Patent: Dec. 26, 2006

(54) WATER-IN-OIL EMULSION AND ITS USE AS A COSMETIC

(75) Inventors: Odile Aubrun-Sonneville, Antony (FR); Jean-Thierry Simonnet, Paris (FR)

(73) Assignee: L'Oreal, Paris (FR)

( * ) Notice: Subject to any disclaimer, the term of this patent is extended or adjusted under 35 U.S.C. 154(b) by 306 days.

(21) Appl. No.: 09/903,606

(22) Filed: Jul. 13, 2001

(65) Prior Publication Data
US 2002/0039565 A1 Apr. 4, 2002

(30) Foreign Application Priority Data
Jul. 13, 2000 (FR) ................................. 00 09223

(51) Int. Cl.
*A61K 31/74* (2006.01)
*A61K 31/765* (2006.01)
*A61K 6/00* (2006.01)

(52) U.S. Cl. ............... 424/78.2; 424/78.18; 424/78.19; 424/64; 424/70.1; 424/401; 514/845; 514/880; 514/937; 525/285

(58) Field of Classification Search ................ 424/401, 424/78.2, 78.18, 78.19, 64, 70.1; 514/138, 514/845, 880, 937; 510/136; 525/285
See application file for complete search history.

(56) References Cited

U.S. PATENT DOCUMENTS

| | | | |
|---|---|---|---|
| 3,846,546 A * | 11/1974 | Lachampt et al. .......... 514/783 |
| 3,860,700 A * | 1/1975 | Viout et al. .................... 424/61 |
| 4,369,123 A | 1/1983 | Seiwitz et al. ............... 252/312 |
| 4,606,913 A * | 8/1986 | Aronson et al. ............... 424/59 |
| 4,698,065 A | 10/1987 | Hoeffkes et al. ................ 8/406 |
| 4,705,682 A | 11/1987 | Moeller et al. ................ 424/70 |
| 4,708,753 A * | 11/1987 | Forsberg ..................... 149/105 |
| 5,401,341 A * | 3/1995 | Forsberg et al. ......... 149/108.8 |
| 5,541,341 A | 7/1996 | Vermeer et al. ............. 548/517 |
| 5,631,389 A | 5/1997 | Vermeer et al. ............. 549/417 |
| 5,650,158 A | 7/1997 | Eierdanz et al. ............ 424/401 |
| 5,652,266 A | 7/1997 | Bobier-Rival et al. ...... 514/557 |
| 5,674,511 A | 10/1997 | Kacher et al. .............. 424/401 |
| 5,786,468 A | 7/1998 | Au et al. .................... 536/29.1 |
| 5,980,922 A * | 11/1999 | Mackey et al. ............. 424/402 |

OTHER PUBLICATIONS

Michalun and Michalun, Milady's Skin Care and Cosmetic Ingredients Dictionary, 1st Ed., Milady Publishing Co., Albany, NY, (1994) pp. 143, 144, 180, 225 and 226.*
Knowlton, J. "Emulsion Theory", Poucher's Perfumes, Cosmetics and Soaps, vol. 3, (9th ed., Hilda Butler), 1993, pp 534-5.*
Proceedings vol. 2, 5th World Surfactants Congress, May 29-Jun. 2, 2000, Fortezza da Basso, Firenze.

* cited by examiner

*Primary Examiner*—Sreeni Padmanabhan
*Assistant Examiner*—Gina C. Yu
(74) *Attorney, Agent, or Firm*—Oblon, Spivak, McClelland, Maier & Neustadt, P.C.

(57) ABSTRACT

A composition, comprising, in a physiologically acceptable medium, an aqueous phase dispersed in an oily phase by means of an emulsifier of at least one oligomer or one polymer derived from a polyolefin, comprising a polyolefinic apolar component comprising at least 40 carbon atoms and at least one polar component.

50 Claims, 2 Drawing Sheets

Comparative example diluted in isohexadecane:
E/H emulsion stabilized by Arlacel 1690

Optical microscopy, enlargement x400, Interferential contrast

Optical microscopy, enlargement x400, Interferential contrast

WATER-IN-OIL EMULSION AND ITS USE AS A COSMETIC

BACKGROUND OF THE INVENTION

1. Field of the Invention

The present invention relates to a water-in oil emulsion comprising an oligomer or a polymer derived from a polyolefin, and its use as a cosmetic, dermatological or pharmaceutical composition. It may be intended in particular for skin, lip and nail care, for make-up removal and/or for cleansing the skin, and/or as make-up for the skin and/or the lips. It may be used more particularly for the treatment of dry skin and/or lips and/or sensitive skin.

2. Discussion of the Background

In the cosmetic and dermatological fields, it is common to use creams consisting of a water-in-oil (W/O) emulsion comprising aqueous globules dispersed in an oily phase. These emulsions comprise a continuous oily phase and therefore make it possible to form, at the surface of the skin, a lipid film which prevents transepidermal water loss, protects the skin from external attacks and can also increase the persistence of sunscreen. Water-in-oil emulsions also make it possible to protect and to carry hydrophilic active agents sensitive to oxidation. These emulsions are particularly appropriate for the care and the repair of dry and dehydrated skin to which they provide comfort and protection by virtue of the lipid barrier which they form on the skin.

However, despite their great efficacy, W/O emulsions constitute a minority of the galenic forms used in the cosmetic field because they pose two major problems. First of all, these emulsions have the disadvantage of generally lacking cosmetic pleasantness, that is to say, they are greasy, heavy, sticky and lack a fresh sensation because of the oily outer phase. They are generally difficult to apply to the skin, they penetrate with difficulty and they leave a shiny and often sticky residual film on the skin.

Moreover, W/O emulsions exhibit problems of stability, in particular when the aqueous phase is in a large quantity or when the emulsion is fluid (consistency of a milk rather than of a cream). The drops of aqueous phase have, in this case, the tendency to aggregate and to form lumps which are visible under a microscope. This aggregation is detrimental to the stability of the emulsions; it promotes, on the one hand, creaming or sedimentation of the fluid systems, and, on the other hand, the coalescence of the drops, leading to the appearance of water domains, that is to say drops of aqueous phase greater than 50 microns in size. It is often necessary, to stabilize these emulsions, to use a high level of emulsifier and/or to introduce a certain quantity of consistency factors such as waxes. However, these ingredients contribute towards increasing the cosmetic defects (gummy and greasy effect) of the W/O emulsions resulting in compositions being obtained which are often compact and heavy. Moreover, in the presence of these consistency factors, it is difficult to obtain fluid emulsions, because these factors thicken the emulsions. Furthermore, if the content of emulsifier in these emulsions is greatly increased to remedy their instability, the emulsions obtained may prove irritant towards certain types of skin, in particular sensitive skin.

Thus, a large number of water-in-oil emulsions exist which are stabilized by various surfactants, in particular alkylated derivatives of polyglycerol, alkylated polyethylene glycols, alkylated derivatives of sorbitan, metal salts of fatty acids and silicone surfactants. However, in the majority of the emulsions stabilized by hydrocarbon-containing surfactants, the content of aqueous phase should remain less than 80% by weight and the level of surfactant should be relatively high, so as to be able to produce an emulsion with acceptable stability. Moreover, it is generally necessary to increase the viscosity of the oily phase by adding waxes (see for example DE 3 430 256), oily gelling agents (see for example EP 0 795 321) or modified clays (see for example EP 0 331 833) in order to improve the stability of the emulsions. The products resulting therefrom often lack a sensation of freshness and lightness.

In addition, silicone surfactants can improve the cosmetic properties of water-in-oil emulsions. However, the sense of feel remains characteristic of silicones, and silicone oils generally have to be the predominant constituents of the oily phase. Moreover, generally, it is necessary to couple these surfactants with at least one other surfactant, most often a hydrocarbon containing surfactant, in order to make the stability of the emulsion perfect. A need therefore remains for a stable water-in-oil emulsion which does not exhibit the disadvantages encountered of conventional and known water-in-oil emulsions, in particular for an emulsion with a light and fresh feel, containing no silicone surfactant and which may be fluid and/or which may have a high content of aqueous phase and which exhibits good stability, even in the absence of factors for which enhance the consistency of the oily phase, in particular even in the absence of waxes.

SUMMARY OF THE INVENTION

Accordingly, one object of the present invention is to provide a composition in the form of a water-in-oil emulsion having good cosmetic properties, particularly including a simultaneously light, fresh and rich feel, and good stability.

Another object of the invention is to provide a water-in-oil emulsion which is very rich in the aqueous phase (more than 80%) and which is of low viscosity and is stable.

Briefly, these objects and other objects as hereinafter will become more readily apparent can be attained by a water-in-oil emulsion composition, comprising, in a physiologically acceptable medium, an aqueous phase dispersed in an oily phase by means of an emulsifier of at least one oligomer or one polymer derived from a polyolefin, comprising a polyolefinic apolar component comprising at least 40 carbon atoms and at least one polar component.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
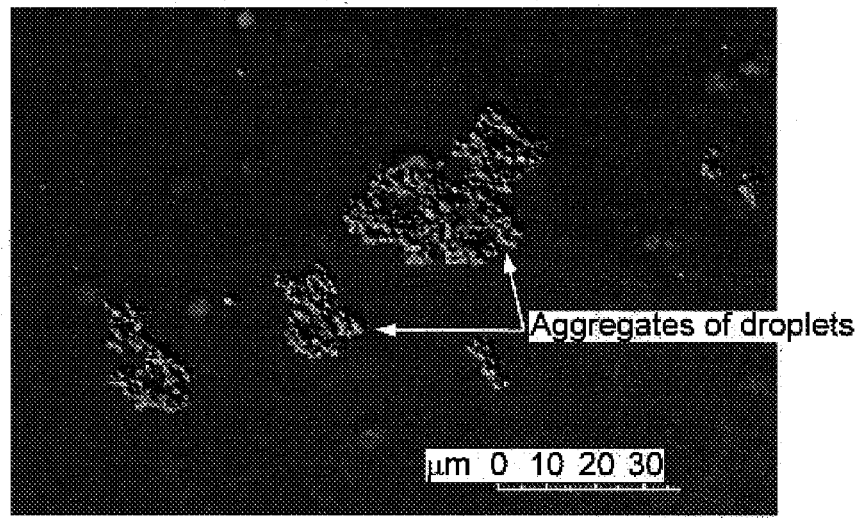
FIGS. 1A and 1B are optical microscopic photographs of diluted emulsions of the formulation, respectively, of Comparative Example 1 and Example 1.

In the present text, the expression "physiologically acceptable medium" is understood to mean a medium compatible with the skin and/or the mucous membranes (lips).

The oligomers and polymers which can be used in the invention are known in other fields. They have been described as stabilizers of explosive emulsions, which are reversed emulsions of molten ammonium nitrate or of a saturated solution of ammonium nitrate in a hydrocarbon oil. In these emulsions, the inner phase contains at most 15% by weight of water (see, for example, U.S. Pat. Nos. 4,234,435 and 4,708,875).

Moreover, these oligomer and polymer compounds are known as stabilizers or fertilizing compositions in the form of a water-in-oil emulsion (see U.S. Pat. No. 5,518,517) in order to obtain controlled release of the fertilizing substances. The inner phase consists of at least 70% by weight of fertilizing agents and at most 30% by weight of water.

In the W/O emulsions described in these prior art documents the aqueous inner phase contains substances specific to the field of application of the composition, such as explosives and fertilizing agents, solubilized or dispersed in a small amount of water. These documents neither describe nor suggest that these polyolefin derivatives can make it possible to obtain water-in-oil emulsions containing a high proportion of water and of cosmetic, dermatological and/or pharmaceutical substances, dispersed or solubilized in this same large quantity of water, to give a fresh composition, which can be applied by the topical route in particular to the skin, and which is stable.

The use of oligomers or polymers derived from polyolefins as emulsifiers in the composition of the invention makes it possible to prepare water-in-oil emulsions that constitute stable compositions of low viscosity, as well as compositions having good stability, although very rich in aqueous phase, i.e., greater than 80% by weight, and in particular rich in water, i.e. at least 30% by weight of water, preferably at least 40% and better still at least 60% by weight of water, relative to the total weight of the composition. The stabilization of these compositions does not require structuring agents of the oily phase such as waxes, polymers or modified clays, or combination with another surfactant. The quantities of emulsifiers used are relatively low. In addition, these emulsifiers promote the production of fresh and light compositions.

An aspect of the present invention is also the use of at least one oligomer or one polymer derived from a polyolefin, comprising a polyolefinic apolar component comprising at least 40 carbon atoms and at least one polar component, for the preparation of a W/O emulsion comprising, in a physiologically acceptable medium, at least 30% by weight of water relative to the total weight of the composition.

The stability of the emulsions of the invention results in good dispersion of the aqueous phase in the oily phase and the absence of aggregates of aqueous droplets, promoting the appearance of water domains of high diameter. The behavior of the emulsion may be demonstrated by a simple test of diluting the emulsion with oil, followed by its observation under a microscope, as described below in the examples. In most cases, the drops aggregate and form masses, which promote the sedimentation and the formation of water domains; the emulsion is then considered to be unstable because of its heterogeneity created by the presence of these water domains. In fact, however, to the opposite, a good dispersion of the droplets of aqueous phase and a good stability of the emulsion, which is homogeneous, is observed in the present invention.

Thus, even in the absence of waxy compounds from the oily phase, the emulsions of the invention may have a cream or fluid texture while having good stability. The viscosity of the emulsions may vary to a large extent and may range in particular from 1 to 150 poises (0.1 Pa.s to 15 Pa.s), these viscosities being measured at about 25° C. with the aid of the "Mettler Rheomat" viscometer which is generally equipped with a No. 2 rotor for viscosity ranges of less than 7 poises, with a No. 3 rotor for viscosity ranges of 2 to 40 poises, and with a No. 4 rotor for viscosity ranges of 20 poises to 80 poises.

The oligomer and polymer emulsifiers in the composition of the present invention consist of a polyolefinic apolar component and of at least one polar component. They can have a block or comb type structure.

The polyolefinic apolar component of the surfactant comprises at least 40 carbon atoms and preferably from 60 to 700 carbon atoms. It is important that this component comprise at least 40 carbon atoms in order to achieve the objective of the invention. If there are less than 40 carbon atoms, a very stable system is not obtained. This apolar component may be selected from polyolefins such as oligomers, polymers and/or copolymers of ethylene, propylene, 1-butene, isobutene, 1-pentene, 2-methyl-1-butene, 3-methyl-1-butene, 1-hexene, 1-heptene, 1-octene, 1-decene, 1-undecene, 1-dodecene, 1-tridecene, 1-tetradecene, 1-pentadecene, 1-hexadecene, 1-heptadecene and 1-octadecene. These polyolefins are hydrogenated or not hydrogenated.

Moreover, the oligomers or polymers derived from the polyolefins which are used in the composition of the invention comprise at least one polar component. This polar component confers amphiphilic properties on the polyolefin derivatives. Thus, these oligomers or polymers reduce the water/oil, i.e. aqueous phase/oily phase, interfacial tension by at least 10 mN/m when they are present at a concentration of 0.01% by weight relative to the total weight of the oily phase. For example, the polyolefin with a succinate terminal group, as described below and marketed under the name L2724 by the company Lubrizol, at a concentration of 0.01% by weight relative to the total weight of the oily phase, reduces the interfacial tension by 15 mN/m at the interface of an aqueous phase consisting of a 1% aqueous solution of $MgSO_4$, and of an oily phase comprising a mixture of oils (isohexadecane/hydrogenated polyisobutene/volatile silicone in a ratio of 8/6/4).

The polar component of the oligomeric or polymeric emulsifier of the invention may be anionic, cationic, nonionic, zwitterionic or amphoteric. The polar component, for example, consists of polyalkylene glycols or of polyalkyleneimines, or of carboxylic or dicarboxylic acids, of anhydrides thereof or of derivatives thereof, and mixtures thereof. Oligomeric or polymeric emulsifiers with a polar carboxylic acid component may be, for example, derived from the reaction of a polyolefin and at least one carboxylic acid or anhydride selected from the group consisting of maleic acid, maleic anhydride, fumaric acid, itaconic acid, citraconic acid, mesaconic acid or aconitic acid. Preferably, the polar component consists of succinic acid or anhydride, ester or amide derivatives thereof, the corresponding salts of alkali metals, alkaline-earth metals or organic salts, or alternatively of polyoxyethylene.

The emulsifiers derived from polyoxyethylene may be, for example, selected from polyisoprenepolyoxyethylene diblock polymers, (polyethylene-copropylene)polyoxyethylene polymers and mixtures thereof. These polymers are described in the publication by Allgaier, Poppe, Willner, Richter (Macromolecules, 1997, Vol. 30, pp. 1582–1586).

The emulsifiers derived from succinic acid or anhydride may be selected, in particular, from the polyolefin derivatives of the succinic acid or anhydride described in U.S. Pat. Nos. 4,234,435; 4,708,753; 5,129,972 and 4,931,110; GB-A-2,156,799 and U.S. Pat. No. 4,919,179 incorporated herein by reference. The polyolefin component may consist, for example, of polyisobutylene, hydrogenated or unhydrogenated, having a molecular weight ranging from 400 to 5000. In the polyisobutylene having a terminal succinic group thus obtained, the succinic component may be esterified, amidated or in the form of a salt, that is to say that, it may be modified by alcohols, amines, alkanolamines or polyols, or may be present in the form of salts of an alkali metal, alkaline-earth metal or ammonium ion or of an organic base such as the salt of diethanolamine or triethanolamine. The polyolefins with an esterified or amidated succinic terminal group are products of the reaction of (a) a polyolefin having a succinic terminal group, and (b) an amine or an alcohol, thereby forming an amide or an ester. The term "amine" as used here comprises all types of amines including alkanol amines. The amines may include, for example, primary, secondary or tertiary monoamines, it being possible for these amines to be aliphatic, cycloaliphatic, aromatic, heterocyclic, saturated or unsaturated. Moreover, the alcohols may be mono- or polyalcohols. The monoalcohols comprise the primary, secondary or tertiary aliphatic alcohols, and phenols. The polyalcohols may be, for example, selected from aliphatic, cycloaliphatic, aromatic and heterocyclic polyalcohols. Polyolefins with a modified (esterified or amidated) succinic terminal group and their method of preparation are described, in particular, in U.S. Pat. No. 4,708,753 which is incorporated herein by reference.

Suitable polyolefins having a succinic terminal group include, in particular, polyisobutylene having a modified succinic terminal group, such as the products marketed under the names L2724 and L2721 by the company Lubrizol.

Another example of a polymeric surfactant which can be used in the invention is the product of the reaction of maleic anhydride with polyisobutylene, such as the product marketed under the name Glissopal SA by the company BASF.

The quantity of emulsifying oligomer(s) or polymers) in the composition of the invention may range, for example, from 0.1% to 10% by weight of active substance, preferably from 0.5% to 5% by weight and even better from 1% to 3% by weight relative to the total weight of the composition. It is possible to use one or more oligomers or polymers derived from polyolefins. According to a preferred embodiment of the invention, the oligomers or polymers derived from polyolefins are the only emulsifiers used in the composition. However, it is possible, where appropriate, to add other amphiphilic agents normally used in water-in-oil emulsions, such as conventional ionic, nonionic, amphoteric or zwitterionic surfactants, amphiphilic oligomers or polymers, amphiphilic organic or inorganic particles.

The quantity of aqueous phase in the emulsion of the invention is preferably at least 40% by weight relative to the total weight of the composition. The quantity may range, for example, from 40% to 95% by weight, preferably from 50% to 90%, better still from 60% to 90% by weight and even better from 80% to 90% by weight relative to the total weight of the composition. The composition of the invention preferably contains at least 30% by weight of water and better still at least 50% by weight of water, relative to the total weight of the composition. The aqueous phase comprises water and all water-soluble or water-dispersible adjuvants optionally present, such as for example polyols such as glycerin and glycols, $C_{2-6}$-lower alcohols such as ethanol, polymers such as carbomers and polysaccharides, salts such as magnesium sulfate, magnesium or sodium chloride, sugars such as glucose and fructose.

The oily phase may comprise all fatty substances conventionally used in the cosmetic field, and in particular oils, and lipophilic additives such as fatty acids, fatty alcohols and gums.

Suitable oils which may be used in the emulsion of the invention include, for example, vegetable oils such as apricot stone oil, avocado oil, macadamia nut oil, sunflower oil, olive oil and soyabean oil; mineral oils such as liquid paraffin; synthetic oils such as hydrogenated polyisobutene, esters of fatty acids and fatty alcohols (as $C_6$–$C_{30}$), ethers of fatty alcohols (as saturated and/or branched $C_4$ to $C_{30}$ fatty alcohols); silicone oils, in particular volatile cyclomethicone oils, such as cyclotetradimethylsiloxane or cyclotetramethicone, cyclopentadimethylsiloxane or cyclopentamethicone, cyclohexadimethylsiloxane or cyclohexamethicone; fluorinated oils and mixtures thereof.

According to a particular embodiment of the invention, the oily phase of the emulsion of the invention contains at least 50% of one or more hydrocarbon oils, that is to say of oils comprising only carbon and hydrogen, which may be volatile or nonvolatile and may be mineral or synthetic. Suitable hydrocarbon oils include, for example, squalane, hydrogenated polyisobutene and hydrocarbon oils with a branched chain which preferably comprise from 6 to 20 and better still from 6 to 18 carbon atoms and may be selected, for example, from the group comprising isohexadecane, isododecane, isoparaffins and mixtures thereof.

When the emulsion is used as a make-up removing product for the skin and/or the eyes, it contains, more particularly, make-up-removing oils and in particular those selected from fatty acid esters comprising at least 12 carbon atoms. These esters are preferably obtained from a straight or branched chain alcohol comprising from 1 to 17 carbon atoms and from a straight or branched chain fatty acid comprising at least 12 carbon atoms, preferably from 14 to 22 carbon atoms. Preferred are mono- or diesters. The make-up-removing oils may be selected in particular from the group comprising 2-ethylhexyl palmitate (or octyl palmitate), 2-ethylhexyl myristate (or octyl myristate), isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate, and mixtures thereof.

The oily phase may also contain waxes, silicone gums, oily gelling agents, organic and/or inorganic particles.

The quantity of oily phase in the emulsion of the invention may range, for example, from 2.5% to 60%, preferably from 5% to 50% and better still from 7.5% to 40% by weight relative to the total weight of the composition. The hydrocarbon oil(s) may represent all or part of this oily phase, and they preferably represent at least 40% by weight relative to the total weight of the oily phase.

The composition of the invention is a W/O emulsion. This emulsion may be used as it is or may be used for the preparation of a multiple W/O/W emulsion by incorporating the primary W/O emulsion into an outer aqueous phase. Thus, the oligomers or polymers derived from a polyolefin which are described above may also be used as emulsifiers for a multiple W/O/W emulsion.

Moreover, they may also be used as emulsifiers for a multiple O/W/O emulsion prepared by incorporating an O/W emulsion into an oily phase containing one or more oligomers or polymers derived from a polyolefin.

Another objective of the present invention is the use of at least one oligomer or one polymer derived from a polyolefin, comprising a polyolefinic apolar component comprising at least 40 carbon atoms and at least one polar component for the preparation of a multiple W/O/W or O/W/O emulsion.

The composition of the invention may constitute, in particular, a cosmetic, dermatological or pharmaceutical composition and more particularly a cosmetic composition intended for application to the skin and/or the mucous membranes.

In a known manner, the composition of the invention may also contain customary adjuvants in the cosmetic and/or dermatological field, other than those mentioned above, such as solvents, active agents, preservatives, antioxidants, complexing agents, perfumes, fillers, bactericides, odor absorbers, coloring matter and lipid vesicles. The quantities of these various adjuvants are those conventionally used in the field considered, and are, for example, from 0.01% to 20% of the total weight of the composition. These adjuvants, depending on their nature, may be introduced into the fatty phase, into the aqueous phase and/or into the lipid vesicles. Of course persons skilled in the art will be careful to choose the possible additional additives and/or their quantity such that the advantageous properties of the composition of the invention are not or not substantially adversely affected by the addition envisaged.

Suitable active agents, which may be included, in particular, in addition to those indicated above, are moisturizers and for example protein hydrolysates and polyols such as glycerin, glycols such as polyethylene glycols, and sugar derivatives; natural extracts; procyannidolic oligomers; vitamins, urea; caffeine; depigmenting agents such as kojic acid and caffeic acid; beta-hydroxy acids such as salicylic acid and its derivatives; alpha-hydroxy acids such as lactic acid and glycolic acid; retinoids such as retinol and its derivatives and carotenoids; organic and inorganic screening agents; hydrocortisone; DHEA; melatonin; algal, fungal, plant, yeast or bacterial extracts; proteins, hydrolysed, partially hydrolysed or unhydrolyzed; enzymes and mixtures thereof.

The active agent(s) may, for example, be present in a concentration ranging from 0.01% to 20%, preferably from 0.1% to 5% and better still from 0.5% to 3% of the total weight of the composition.

Advantageously, the emulsion of the invention is prepared by incorporating the aqueous phase into the oily phase comprising the emulsifiers, with stirring, at a temperature preferably ranging from about 20 to 60° C.

The composition of the invention finds application in a large number of treatments, in particular, cosmetic treatments, It may be intended in particular for the treatment of, the protection of, the care of skin, lip and nail care, for make-up removal and/or for cleansing the skin, and/or as make-up for the skin and/or the lips. It may be used more particularly for the treatment of dry skin and/or lips and/or sensitive skin. It may also be used for the application of make-up to the skin and/or lips.

The composition of the invention may, for example, be used as a care, make-up-removing and/or cleansing product for the face in the form of creams or milks or as make-up products (skin and lips), and for example as foundations, by incorporation of fillers and colorants.

Also, the subject of the invention is furthermore the cosmetic use of the composition as defined above for the treatment of, protection of, care of, removal of make-up from, cleansing of and/or application of make-up to the skin and/or the lips.

An aspect of the invention is also a method for the cosmetic treatment of the skin and/or the lips, wherein a composition as defined above is applied to the skin and/or the lips.

Still another aspect of the invention is the use of the composition as defined above for the manufacture of a composition intended for the care of dry skin and/or dry lips and/or sensitive skin.

Having now generally described this invention, a further understanding can be obtained by reference to certain specific examples which are provided herein for purposes of illustration only and are not intended to be limiting unless otherwise specified. The quantities are given therein as % by weight, unless otherwise stated.

EXAMPLE 1

Moisturizing Cream

| Oily phase: | |
|---|---|
| L2724 | 2.5% |
| Isohexadecane | 3.29% |
| Hydrogenated polyisobutene | 2.47% |
| Cyclomethicone | 1.64% |
| Preservative | 0.1% |

| Aqueous phase: | |
|---|---|
| Magnesium sulfate | 0.9% |
| Preservatives | 0.65% |
| Water | 88.45% |

The formulation is provided in the form of a soft cream which is stable for at least two months at a temperature of 4° C. to 45° C.

Comparative Example 1

| Oily phase: | |
|---|---|
| Arlacel 1690 (company ICI) | 2.5% |
| Isohexadecane | 3.29% |
| Hydrogenated polyisobutene | 2.47% |
| Cyclomethicone | 1.64% |
| Preservative | 0.1% |

| Aqueous phase: | |
|---|---|
| Magnesium sulfate | 0.9% |
| Preservatives | 0.65% |
| Water | 88.45% |

The composition is provided in the form of a cream exhibiting numerous water domains, having a size greater than 50 µm (observation under a microscope). This composition is not stable over time.

Comparison of the Stability of the Composition of the Invention (Example 1) Versus a Prior Art Composition (Comparative Example 1):

1) Observation Under a Microscope

A dilution was prepared by diluting a drop of emulsion with 5 ml of isohexadecane.

Figure 1B:
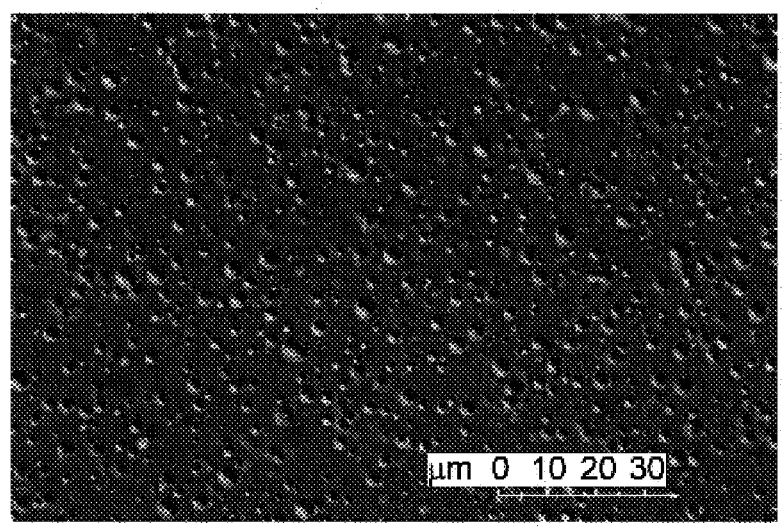

FIG. 1 of the present application shows photos of the emulsion of Comparative Example 1 (FIG. 1A) and that of Example 1 of the invention (FIG. 1B), observed under a microscope after dilution. For Comparative Example 1 (FIG. 1A), masses of globules of aqueous phase (water domains) are observed in the continuous oily phase, whereas, for the composition of Example 1 of the invention (FIG. 1B), a good dispersion of the globules of the aqueous phase in the continuous oily phase is observed. Thus, the use of the mixture of sorbitan isostearate and of polyglyceryl-3 isostearate (Arlacel 1690) in the comparative example does not make it possible to obtain a stable homogeneous dispersion, whereas the use of a polymeric emulsifier (L2724) in the example of the invention makes it possible to obtain a stable and homogeneous dispersion.

2) Rheology

The rheology results also demonstrate the difference between the emulsion of the invention and that of the comparative example, and in particular show the aggregated state of the globules of aqueous phase in the emulsion of the comparative example. The aggregated systems exhibit a viscosity at low stress which is greater than that of non-aggregated systems.

Figure 2:
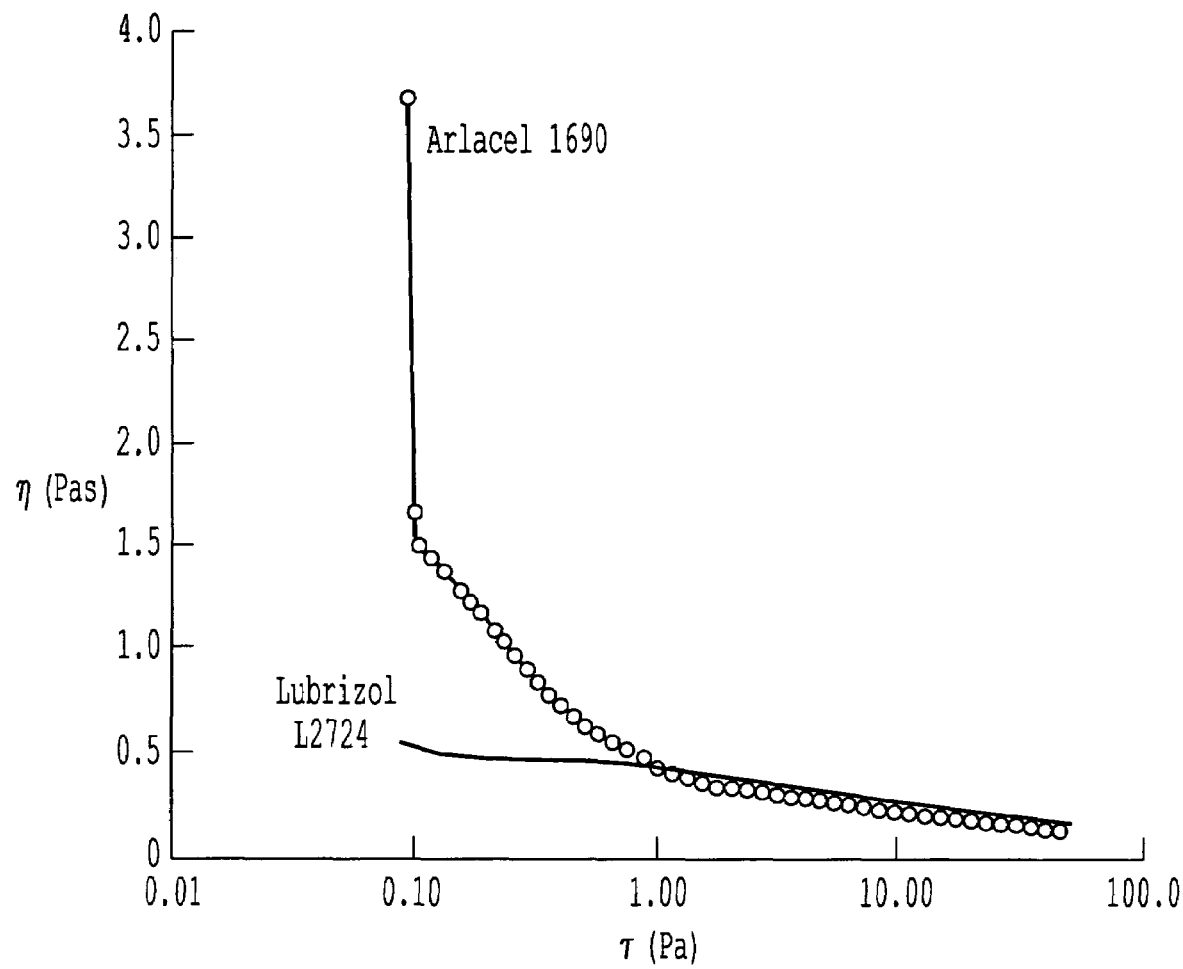
FIG. 2 shows the apparent viscosities of diluted formulations of Example 1 (L2724) and of Comparative Example 1 (Arlacel 1690) as a function of applied stress.

FIG. 2 presents measurements during flow under applied stress of Example 1 of the invention and of Comparative Example 1, after dilution of each emulsion with isohexadecane, a dilution such that the content of aqueous phase is brought to 70% by weight relative to the total composition, so as to better demonstrate the differences in Theological behavior. It is observed that the system with Arlacel 1690 (comparative example) exhibits a viscosity at low stress which is greater than that of the system with L2724. The system with Arlacel 1690 aggregates unlike the system with L2724.

EXAMPLE 2

Moisturizing Milk

| Oily phase: | |
| --- | --- |
| L2721 | 2.21% |
| Isohexadecane | 7.87% |
| Cyclohexamethicone | 3.93% |
| Hydrogenated polyisobutene | 5.9% |
| Preservatives | 0.09% |

| Aqueous phase: | |
| --- | --- |
| Magnesium sulfate | 0.8% |
| Preservatives | 0.58% |
| Water | qs 100% |

The composition is provided in the form of a beige milk having a viscosity of 15.2 poises (1.52 Pa.s) (rotor 3,200 $s^{-1}$), having good stability (stable for at least two months at from 4 to 45° C.).

EXAMPLE 3

Care Cream for Dry Skin

| Oily phase: | |
| --- | --- |
| L2724 | 2.24% |
| Apricot stone oil | 10.24% |
| Isododecane | 6.63% |
| Preservative | 0.09% |

| Aqueous phase: | |
| --- | --- |
| Magnesium sulfate | 0.81% |
| Preservatives | 0.58% |
| Water | qs 100% |

The composition is provided in the form of a soft cream having a viscosity of 44 poises (4.4 Pa.s) (rotor 3,200 $s^{-1}$), which is stable for at least two months at a temperature of 4 to 45° C.

The disclosure of French priority Application Number 0009223 filed Jul. 13, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed is:

1. A physiologically acceptable composition, comprising: an aqueous phase dispersed in an oily phase, and an oligomeric or polymeric emulsifier comprising i) a polyolefinic apolar component comprising at least 40 carbon atoms and ii) at least one polar component, wherein said oily phase comprises at least one hydrocarbon oil and said at least one hydrocarbon oil is present in an amount of at least 40% by weight relative to the total weight of the oily phase.

2. The composition according to claim 1, wherein the polyolefinic apolar component of the emulsifier comprises from 60 to 700 carbon atoms.

3. The composition according to claim 2, wherein the polyolefinic apolar component of the emulsifier is selected from the group consisting of oligomers, polymers and/or copolymers of ethylene, propylene, 1-butene, isobutene, 1-pentene, 2-methyl-1-butene, 3-methyl-1-butene, 1-hexene, 1-heptene, 1-octene, 1-decene, 1-undecene, 1-dodecene, 1-tridecene, 1-tetradecene, 1-pentadecene, 1-hexadecene, 1-heptadecene and 1-octadecene.

4. The composition according to claim 1, wherein the emulsifier reduces the interfacial tension between the aqueous phase and the oily phase of the emulsion by at least 10 mN/m when said emulsifier is present at a concentration of 0.01% by weight relative to the weight of the oily phase.

5. The composition according to claim 1, wherein the polar component of the emulsifier is anionic, cationic, nonionic, zwitterionic or amphoteric.

6. The composition according to claim 5, wherein the polar component of the emulsifier is selected from the group consisting of polyalkylene glycols, polyalkyleneimines, carboxylic acids, dicarboxylic acids, anhydrides and mixtures thereof.

7. The composition according to claim 6, wherein the polar component of the emulsifier is selected from the group consisting of polyoxyethylene, succinic acid and succinic anhydride.

8. The composition according to claim 1, wherein the emulsifier is prepared by the reaction of a polyolefin compound and at least one acid selected from the group consisting of maleic acid, maleic anhydride, fumaric acid, itaconic acid, citraconic acid, mesaconic acid, aconitic acid and mixtures thereof.

9. The composition according to claim 1, wherein the emulsifier is a polyisobutylene with an optionally modified succinic terminal group.

10. The composition according to claim 8, wherein the emulsifier is the product of the reaction of maleic anhydride with polyisobutylene.

11. The composition according to claim 1, wherein the amount of emulsifier present ranges from 0.1% to 10% by weight relative to the total weight of the emulsion.

12. The composition according to claim 1, wherein the quantity of aqueous phase ranges from 40% to 95% by weight relative to the total weight of the composition.

13. The composition according to claim 1, wherein the composition comprises at least 1% by weight of water relative to the total weight of the composition.

14. The composition according to claim 1, wherein the quantity of oily phase ranges from 2.5% to 60% by weight relative to the total weight of the composition.

15. A physiologically acceptable cosmetic emulsion composition, comprising:
an aqueous phase dispersed in an oily phase, and an oligomeric or polymeric emulsifier comprising i) a polyolefinic apolar component comprising at least 40 carbon atoms and ii) at least one polar component, wherein said oily phase comprises at least one hydrocarbon oil and said at least one hydrocarbon oil is present in an amount of at least 40% by weight relative to the total weight of the oily phase.

16. A method of cosmetic treatment, comprising:
applying the composition of claim 15 to the skin or the lips thereby effecting the treatment of, protection of, care of, removal of make-up from, cleansing of and/or application of make-up to the skin and/or the lips.

17. A cosmetic composition for the care of dry skin, dry lips and/or sensitive skin, comprising:
the composition of claim 1 and at least one cosmetic adjuvant thereby providing for the effective care of dry skin, dry lips and/or sensitive skin.

18. A method of manufacturing a physiologically acceptable cosmetic W/O emulsion composition, comprising;
combining a physiologically acceptable aqueous medium in an amount such that water component of the cosmetic composition is at least 30% by weight of water relative to the total weight of the composition and an oily phase in the presence of at least one oligomeric or polymeric emulsifier comprising i) a polyolefinic apolar component comprising at least 40 carbon atoms and ii) at least one polar component, wherein said oily phase comprises at least one hydrocarbon oil and said at least one hydrocarbon oil is present in an amount of at least 40% by weight relative to the total weight of the oily phase.

19. The method according to claim 18, wherein said content of water is at least 50% by weight in the composition.

20. A method of preparing a multiple W/O/W or O/W/O emulsion, comprising:
combining the prepared composition of claim 1 with water or oil to prepare a W/O/W rnulsion or a O/W/O emulsion.

21. A make-up removing composition, comprising:
the composition of claim 1 in combination with a make-up removing oil.

22. The make-up removing composition according to claim 21, wherein said make-up removing oil is a fatty acid ester of a straight or branched $C_{1-17}$-alcohol and a straight or branched fatty acid of at least 12 carbon atoms.

23. The composition according to claim 1, wherein the composition comprises at least 80% by weight of aqueous phase relative to the total weight of the composition.

24. The composition according to claim 1, wherein the composition comprises at least 80% by weight of aqueous phase and at least 30% by weight of water relative to the total weight of the composition.

25. The composition according to claim 15, wherein the composition comprises at least 80% by weight of aqueous phase relative to the total weight of the composition.

26. The composition according to claim 15, wherein the composition comprises at least 30% by weight of water relative to the total weight of the composition.

27. The composition according to claim 15, wherein the composition comprises at least 80% by weight of aqueous phase and at least 30% by weight of water relative to the total weight of the composition.

28. The composition according to claim 1, wherein the composition is a topical composition.

29. The composition according to claim 11, wherein the composition is a topical composition.

30. The composition according to claim 12, wherein the composition is a topical composition.

31. The composition according to claim 13, wherein the composition is a topical composition.

32. The composition according to claim 28, wherein the composition comprises at least 30% by weight of water relative to the total weight of the composition.

33. The composition according to claim 29, wherein the composition comprises at least 30% by weight of water relative to the total weight of the composition.

34. The composition according to claim 30, wherein the composition comprises at least 30% by weight of water relative to the total weight of the composition.

35. The composition according to claim 28, wherein the quantity of aqueous phase ranges from 40% to 95% by weight relative to the total weight of the composition.

36. The composition according to claim 29, wherein the quantity of aqueous phase ranges from 40% to 95% by weight relative to the total weight of the composition.

37. The composition according to claim 34, wherein the quantity of oligomeric or polymeric emulsifier present ranges from 0.1% to 10% by weight relative to the total weight of the composition.

38. A physiologically acceptable topical composition, comprising:
an aqueous phase dispersed in an oily phase, and an oligomeric or polymeric emulsifier comprising i) a polyolefinic apolar component comprising at least 40 carbon atoms and ii) at least one polar component, wherein the composition comprises at least 30% by weight of water relative to the total weight of the composition, the quantity of aqueous phase ranges from 40% to 95% by weight relative to the total weight of the composition, the quantity of emulsifier present ranges from 0.1% to 10% by weight relative to the total weight of the composition, said oily phase comprises at least one hydrocarbon oil and said at least one hydrocarbon oil is present in an amount of at least 40% by weight relative to the total weight of the oily phase.

39. The composition according to claim 1, wherein the quantity of oligomeric or polymeric emulsifier present ranges from 0.5% to 5% by weight relative to the total weight of the composition.

40. The composition according to claim 15, wherein the quantity of oligomeric or polymeric emulsifier present ranges from 0.5% to 5% by weight relative to the total weight of the composition.

41. The composition according to claim 38, wherein the quantity of oligomeric or polymeric emulsifier present ranges from 0.5% to 5.0% by weight relative to the total weight of the composition.

42. The composition according to claim 1, wherein the quantity of oligomeric or polymeric emulsifier present ranges from 1% to 3% by weight relative to the total weight of the composition.

43. The composition according to claim 15, wherein the quantity of oligomeric or polymeric emulsifier present ranges from 1% to 3% by weight relative to the total weight of the composition.

44. The composition according to claim 38, wherein the quantity of oligomeric or polymeric emulsifier present ranges from 1% to 3% by weight relative to the total weight of the composition.

45. The composition according to claim 1, wherein the emulsification system of the composition consists essentially of said oligomeric or polymeric emulsifier.

46. The composition according to claim 15, wherein the emulsification system of the composition consists essentially of said oligomeric or polymeric emulsifier.

47. The composition according to claim 38, wherein the emulsification system of the composition consists essentially of said oligomeric or polymeric emulsifier.

48. The composition according to claim 1, wherein the composition is stable at 40° C. for at least two months.

49. The composition according to claim 1, wherein the composition is stable at 25° C. for at least two months.

50. The composition according to claim 1, wherein the composition is stable at 45° C. for at least two months.

* * * * *